United States Patent [19]

Mikkelsen

[11] Plant 5,184

[45] Jan. 31, 1984

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 354,072

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Corona and characterized by its large plant size and vigorous, self-branching growth habit; dark pink to red-purple flower color; excellent keeping qualities of flowers thereby making cultivar excellent for indoor use; relatively large green leaves with mid-rib veination, and by its adaptability to various environments of use.

1 Drawing Figure

The present invention relates to a new and distinctive cultivar of Impatiens plant, botanically known as Impatiens and known by the cultivar name Corona. The new cultivar was developed by me through controlled breeding in Ashtabula, Ohio. The seed parent was 79-1082-4 (Mikkelsen) and the pollen parent was 79-1164-1 (Mikkelsen). Asexual reproduction of terminal or stem cuttings has shown that the unique features of this new impatiens are stabilized and are reproduced true to type in successive propagations.

The following characteristics distinguish Corona from both its parent varieties and other cultivated impatiens of this type known and used in the floriculture industry:

1. Larger, more vigorous growing plant than the cultivars Columbia, Gemini, Flare, or Solared, all of which are disclosed in other pending applications of applicant.

2. Flower color is a deeper pink than Columbia or Gemini. The flower color is considerably deeper in winter in the greenhouse with low light.

3. Flowers have excellent keeping qualities, and nestle in the foliage as they mature, similar to the flowering habit of Columbia.

4. The new cultivar is self-branching, a vigorous grower, somewhat procumbent yet having vigorous stems, and is ideal for small pots, baskets and bedding plant use.

5. Leaf color is nearly same as Columbia but with more mid-rib veination; foliage is larger and more abundant than Columbia.

6. Plant and flowers have good low temperature tolerance when gradually acclimated to outdoors autumn weather. The illustrated specimen was the last plant of the series of new cultivar noted above to be killed by frost.

7. Flowering begins somewhat slower than Columbia, Gemini, Solared, or Telstar, disclosed in U.S. Plant Pat. No. 4,733.

8. Testing to date indicates Corona to be the best keeping cultivar for indoor use as a small potted flowering plant of all cultivars tested. Individual flowers hold under poor light for upwards to two weeks.

9. An excellent cultivar for further hybridizing for indoor flowering plant use.

The accompanying colored photograph taken in August in full sun outdoors illustrates the overall appearance of Corona, with the flowers being somewhat faded. The photo is a generally top perspective view of the plant, and shows the colors as true as it is reasonably possible to obtain in a colored reproduction of this type.

The following is a detailed description of my new impatiens cultivar based on plants produced under commercial practice in Ashtabula, Ohio. The illustrated specimen as planted outside in full sun the second week of June from a 4" pot. At the time of the picture the single plant was 60 cm. in diameter and 40 cm. tall. Color references are made to the Royal Horticultural Society Colour Chart except where general terms of ordinary dictionary significance are used.

Parentage: Mikkelsen seedling 79-1082-4×Mikkelsen seedling 79-1164-1.

PROPAGATION:

(A) *Stem cuttings.*—Cuttings 15 mm. long will develop to 4–5 cm. long in 18–21 days.

(B) *Time to initiate root.*—8–10 days at 23° C. summer.

*Time to initiate root.*—10–12 days at 20° C. winter.

Plant description:

(A) *Form.*—Symmetrically mounded, compact, self-branching, red stemmed, vigorous growing flowering herb.

(B) *Habit of growth.*—Vigorous, self-branching, compact, mounded, continuous flowering.

(C) *Foliage.*—Broad dark green foliage with some basal variegation. (1) Size: 8–9 cm. long×3.5–4 cm. wide. (2) Shape: Lanceolate to obvate with acuminate apex, acute base. (3) Texture: Rugose upper side, glabrous underside. (4) Margin: Finely serrated, very finely ciliated. (5) Color: Young foliage, top side green 137-A, underside yellow green 147-B; mature foliage, top side between green 135A–136A (summer) and green 137-A (winter); underside winter yellow green 147-B, summer green 137A. Some basal mid-rib variegation. (6) Veination: pinnate.

FLOWERING DESCRIPTION:

(A) *Flowering habits.*—Flowers continuously from leaf whorl in progressively orderly manner, taking 5–7 days from bud to bloom; flowers last 2–3 weeks.

(B) *Natural flowering season.*—Indeterminant and continuous. Quantity of flowering increases with increasing levels of light.

(C) *Flower buds.*—Ellipsoidal, flowers perfect, red spur 5 cm. long with throat behind ovary and originating from the major sepal.

(D) *Flowers borne.*—Individual short pedicels from whorl of 5–6 leaves, flowering progressively around the whorl as leaves and buds develop, and remaining within the leaf canopy.

(E) *Quantity of flowers.*—Quite floriferous; flowering development is continuous so that tight buds to mature blooms are visible at the same time in large numbers.

(F) *Petals.*—(1) Shape: Heart-shaped, top dominant, 4 overlapping and symmetrical. (2) Color, top side, winter red purple 72-B, underside 72B-C, top side in summer when opening, red purple 68A-B, with bright red eye surrounding the ovary, top side fading to red purple 68C-D; underside 68-C. (3) Number of petals: Five (5). (4) Size of flowers: 5–5.5 cm. in diameter.

(G) *Reproductive organs.*—(1) Stamens: Five (5) in number. a. Anther shape, hooded; color, red purple 68-B summer. b. Pollen color, cream. (2) Pistils a. Stigma: Five (5) in number, segmented column-shaped, white in color. b. Style color: Clear. c. Ovaries: Five (5) in number, celled; size 5 mm. until fertilized, green in color.

Disease resistance: No significant disease or insect problems seen to date:

9n

I claim:

1. A new and distinct cultivar of impatiens plant known by the cultivar name Corona, as described and illustrated, and particularly characterized by its large plant size and vigorous, self-branching growth habit; dark pink to red-purple flower color; excellent keeping qualities of flowers thereby making cultivar excellent for indoor use; relatively large green leaves with midrib veination, and by its adaptability to various environments of use.

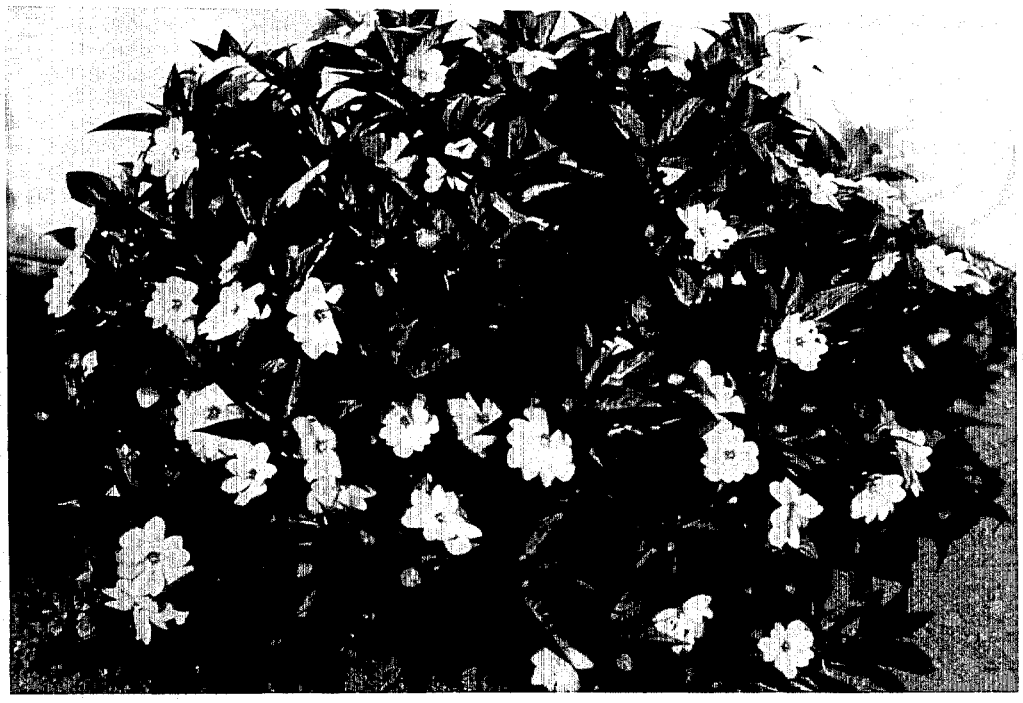

* * * * *